(12) United States Patent
Moudy

(10) Patent No.: US 10,736,802 B1
(45) Date of Patent: *Aug. 11, 2020

(54) LEG SUPPORT

(71) Applicant: Creative Medical Devices LLC, Phoenix, AZ (US)

(72) Inventor: Joanne Moudy, Phoenix, AZ (US)

(73) Assignee: CREATIVE MEDICAL DEVICES LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/806,897

(22) Filed: Mar. 2, 2020

Related U.S. Application Data

(63) Continuation of application No. 16/562,621, filed on Sep. 6, 2019, now Pat. No. 10,617,584.

(51) Int. Cl.
| | | |
|---|---|---|
| *A61G 7/075* | (2006.01) | |
| *A61G 7/057* | (2006.01) | |
| *A61B 5/00* | (2006.01) | |
| *A61G 13/12* | (2006.01) | |

(52) U.S. Cl.
CPC .......... *A61G 7/0755* (2013.01); *A61G 7/057* (2013.01); *A61B 5/447* (2013.01); *A61G 13/1245* (2013.01); *A61H 2201/0142* (2013.01)

(58) Field of Classification Search
CPC .. A47C 20/021; A61G 7/0755; A61G 13/123; A61G 13/1245; A61G 5/00; A61B 6/04
USPC ...................................................... 128/845
See application file for complete search history.

(56) References Cited

U.S. PATENT DOCUMENTS

| | | | | | |
|---|---|---|---|---|---|
| 2,709,435 | A | * | 5/1955 | Kress | A61G 7/0755 604/293 |
| 2,960,151 | A | * | 11/1960 | Fairgrieve | A47C 20/021 297/423.41 |
| 3,104,446 | A | * | 9/1963 | Throop, Jr. | A61G 17/04 27/21.1 |
| 3,604,023 | A | * | 9/1971 | Lynch | A47C 20/021 5/650 |
| 3,639,929 | A | * | 2/1972 | Ichise | A47C 20/021 5/648 |
| 3,783,863 | A | * | 1/1974 | Kliever | A61B 6/0421 128/847 |
| 3,803,645 | A | * | 4/1974 | Oliverius | A47C 20/00 5/650 |
| 3,946,451 | A | * | 3/1976 | Spann | A61G 7/0755 5/650 |
| 4,090,268 | A | * | 5/1978 | Turner | A47C 16/02 297/423.41 |

(Continued)

Primary Examiner — Eric J Kurilla
(74) Attorney, Agent, or Firm — John J. Bamert, Esq.; Lowe Graham Jones PLLC

(57) ABSTRACT

A leg support system includes an ankle cradle for preventing or mitigating pressure ulcers on heels of a patient supported on a top surface of a medical support platform. The ankle cradle includes a cradle base, a first ankle support, and a second ankle support. The cradle base has a bottom surface and is sized and dimensioned to be supported on the top surface of the medical support platform, with the bottom surface of the cradle base contacting the top surface of the medical support platform. The first ankle support is coupled to the cradle base. The second ankle support is spaced apart from the first ankle support and couples to the first ankle support or the cradle base.

19 Claims, 9 Drawing Sheets

(56) References Cited

U.S. PATENT DOCUMENTS

| | | | | |
|---|---|---|---|---|
| 4,854,566 A * | 8/1989 | Broudy | A61B 6/0421 | 269/44 |
| 5,063,918 A * | 11/1991 | Guhl | A61B 17/6425 | 602/40 |
| 5,117,522 A * | 6/1992 | Everett | A61G 7/0755 | 5/644 |
| 5,149,033 A * | 9/1992 | Burzler | A61G 7/0755 | 248/118 |
| 5,745,939 A * | 5/1998 | Flick | A47C 20/021 | 5/490 |
| 6,012,187 A * | 1/2000 | Bushong | A47C 20/021 | 5/612 |
| 6,065,166 A * | 5/2000 | Sharrock | A61G 7/065 | 5/630 |
| 6,085,371 A * | 7/2000 | Umhofer | A61G 7/0755 | 5/648 |
| 6,256,822 B1 * | 7/2001 | Weston | A47C 21/08 | 5/731 |
| 6,442,779 B1 * | 9/2002 | LeVert | A47C 4/54 | 5/648 |
| 6,564,407 B1 * | 5/2003 | Luu | A47C 7/029 | 5/654 |
| 6,634,045 B1 * | 10/2003 | DuDonis | A47C 20/021 | 5/632 |
| 7,036,169 B2 * | 5/2006 | Marshall | A61B 6/0421 | 378/208 |
| 7,235,057 B2 * | 6/2007 | LeVert | A47C 16/025 | 5/648 |
| 8,156,941 B1 * | 4/2012 | Simms | A47C 20/021 | 128/845 |
| 8,176,585 B1 * | 5/2012 | Isham | A61G 13/121 | 5/621 |
| 8,286,286 B2 * | 10/2012 | Al-Saif | A47G 33/008 | 5/420 |
| 8,771,213 B2 * | 7/2014 | Wens | A61F 5/0585 | 128/882 |
| 10,306,991 B2 * | 6/2019 | Behlen | A47C 7/52 | |
| 2001/0016960 A1 * | 8/2001 | Grabell | A47C 20/021 | 5/648 |
| 2003/0182727 A1 * | 10/2003 | DuDonis | A47C 20/021 | 5/648 |
| 2003/0200971 A1 * | 10/2003 | Rastegar | A61H 9/0078 | 128/845 |
| 2004/0093673 A1 * | 5/2004 | Marshall | A61B 6/0421 | 5/650 |
| 2006/0230537 A1 * | 10/2006 | Torres | A47C 20/021 | 5/648 |
| 2007/0094800 A1 * | 5/2007 | Hensley | A47C 20/021 | 5/648 |
| 2008/0178390 A1 * | 7/2008 | DuDonis | A47C 20/021 | 5/632 |
| 2011/0179577 A1 * | 7/2011 | Gould | A61G 5/12 | 5/648 |
| 2012/0180219 A1 * | 7/2012 | Riccabona | A47C 20/021 | 5/636 |
| 2013/0112213 A1 * | 5/2013 | Bhat | A61F 5/00 | 128/889 |
| 2013/0180530 A1 * | 7/2013 | Choi | A61G 7/05776 | 128/889 |
| 2013/0255699 A1 * | 10/2013 | Squitieri | A61F 5/84 | 128/892 |
| 2015/0265061 A1 * | 9/2015 | Spaugh | A61G 13/1245 | 5/505.1 |
| 2019/0247214 A1 * | 8/2019 | Siers | A61G 13/1285 | |

* cited by examiner

US 10,736,802 B1

LEG SUPPORT

CROSS REFERENCE TO RELATED APPLICATION

This application is a continuation of U.S. patent application Ser. No. 16/562,621, filed Sep. 6, 2019, titled "LEG SUPPORT", the entirety of which is incorporated herein by reference.

TECHNICAL FIELD

The present invention relates generally to leg support methods, apparatuses, and systems and, more particularly, yet not exclusively, methods, apparatuses, and systems for supporting legs to prevent or mitigate pressure ulcers.

BACKGROUND

When a patient lays stationary for one or more hours, the patient often develops pressure ulcers on several points of the patient's body (typically bony portions, such has the heels) that contact the surface on which the patient lies. Extended stationary laying occurs in a variety of situations, such as when transporting patients strapped to stretchers or spinal boards from remote areas to metropolitan hospitals, treating patients in medical facilities (for example, catheterization laboratories, operating rooms, intensive care units, observation rooms, inpatient rooms, or others), or caring for bed-ridden patients in their own homes, senior living facilities, or other locations. In fact, more than 2.5 million people in the United States develop pressure ulcers each year, and an estimated 11 billion dollars is spent annually on pressure-ulcer care. Pressure ulcer formation is a leading cause of increased length of hospital stay among surgical patients, further increasing patient suffering and expenses and further consuming limited hospital resources. The problems related to pressure ulcers are so prevalent that, in 2008, Medicare ceased funding and payments to medical facilities related to pressure ulcers that initiated while the patient was hospitalized.

The typical approach to addressing the pressure ulcer problems associated with extended stationary laying is to adhere pads to pressure points on the patient's body, such as the heels. The pads reduce the effects of stationary laying by exposing the pressure points to indirect pressure from the surface on which the patient lies, as opposed to direct pressure from the surface on which the patient lies. The pads typically include gel pads, inflated pads, foam pads, or others. However, the pads typically only delay the onset of pressure ulcers, often by as little as one hour.

Pressure ulcers often present as open wounds that extend through the skin and expose the bone. As a result, once pressure ulcers mature to this stage (often within 3 hours, even when pads are preemptively applied), the patient experiences excruciating pain. This excruciating pain is often experienced following cardiac ablations, for example, where patients must remain stationary for up to 5 or 6 hours during the procedure, 1 to 2 hours during immediately subsequent recovery, and an additional 4 to 6 hours in an observation or inpatient room. To alleviate the pain in the patient's heels, it has been considered to place pillows or rolled towels under their calves or ankles, yet the medical professionals typically strictly prevent such action because it involves movement of the patient that could endanger the patient's recovery and because it changes the angle of the patient's legs, thereby changing the angle of the groin and preventing access to urinary catheters and also preventing "sand bagging" (placement of heavy pressure sand bags on the patient's groin while the femoral veins or arteries clot). Such action is also typically avoided before or during surgery to prevent reducing access to the femoral veins or arteries.

The placement of uncontrolled towels or pillows also interferes with the medical professional's ability to quickly place the patient's body into the desired position for surgery. Placement of towels or pillows under the calves further interferes with sequential compression devices that are often wrapped around the patient's calves to prevent deep vein thrombosis. Commercially available products that may be used instead of towels or pillows typically likewise inhibit the ability of medical professionals to act quickly and confidently during emergencies or medical procedures because they (a) are often unstable to the point where they must be held by hand while the patient's extremity is placed on the product, (b) typically require moving the products subsequent to moving the patient's extremities subsequent to placement of the patient on laying surface to place the products under the patient's extremities, or (c) typically require moving the patient's extremities in conjunction with the products subsequent to placing the products under the patient's extremities to provide a desired groin angle or access to the femoral veins or arteries.

SUMMARY OF THE INVENTION

It is therefore an object of the present invention to provide leg support methods, apparatuses, or systems that facilitate preventing or mitigating pressure ulcers on a patient's heels without adversely influencing groin angle or access to the femoral veins or arteries.

It is also an object of the present invention to provide leg support methods, apparatuses, or systems that achieve the above object without interfering with sequential compression devices on the patient's calves.

It is another object of the present invention to provide leg support methods, apparatuses, or systems that achieve the above objects and that also facilitate increasing stability of the patient's legs.

It is a further object of the present invention to provide leg support methods, apparatuses, or systems that achieve the above objects and that also facilitate increasing the ease at which medical professionals position the patient's legs to obtain a desired groin angle or access to the femoral veins or arteries.

It is yet another object of the present invention to provide leg support methods, apparatuses, or systems that achieve the above objects and that also facilitate guiding medical professionals to position the patient's legs relative to each other to provide unencumbered placement of medical lines between the patient's legs, such as catheters (for example, catheters feeding peripheral venous catheters, catheters feeding central venous catheters, catheters feeding ports implanted in patients, urinary catheters, or other catheters) or wires (for example, stimulation wires, monitor wires, or other wires).

It is yet a further object of the present invention to provide leg support methods, apparatuses, or systems that achieve the above objects and that also facilitate alleviating joint discomfort of the patient.

The invention achieves the above objects, as well as other objects and advantages that will become apparent from the description that follows, by providing a leg support system for preventing or mitigating pressure ulcers on heels of a patient supported on a top surface of a medical support platform. The leg support system includes one or more of a knee support or an ankle cradle.

The knee support includes a support base and an upward-facing support. The support base has a bottom surface and is sized and dimensioned to be supported on the top surface of the medical support platform, with the bottom surface of the support base contacting the top surface of the medical support platform. The upward-facing support is disposed on the support base.

The ankle cradle includes a cradle base, a first ankle support, and a second ankle support. The cradle base has a bottom surface and is sized and dimensioned to be supported on the top surface of the medical support platform, with the bottom surface of the cradle base contacting the top surface of the medical support platform. The first ankle support is coupled to the cradle base. The second ankle support is coupled to the cradle base. The second ankle support is spaced apart from the first ankle support and couples to the first ankle support or the cradle base.

Preferably, the ankle cradle further includes a third ankle support. In some versions, the third ankle support is spaced apart from the first ankle support and the second ankle support. Preferably, the third ankle support couples to the first ankle support, the second ankle support, or the cradle base.

Preferably, the ankle cradle further includes three or more ankle retainers. In some versions, a first pair of the ankle retainers flanks the first ankle support and, most preferably, couples to the first ankle support. Preferably, a second pair of the ankle retainers flanks the second ankle support and, most preferably, couples to the second ankle support.

Preferably, the ankle cradle further includes a shield member. In some versions, the first ankle support and the second ankle support form a cradle member. Preferably, the cradle member has a first side and a second side and is sized and dimensioned such that, when ankles of the patient are supported in the first ankle support and the second ankle support, heels of the patient are suspended on the first side of the cradle member and a torso of the patient is disposed on the second side of the cradle member. In some versions, the shield member couples to the cradle member or the cradle base, is disposed on the first side of the cradle member, and is spaced apart from the first ankle support and the second ankle support.

Preferably, the shield member includes a shield base. In some versions, the cradle base forms a base of the cradle member. Preferably, the shield base of the shield member couples to the cradle base of the cradle member.

Preferably, the cradle member has three or more ankle retainers. In some versions, a first pair of the ankle retainers flanks the first ankle support and, most preferably, couples to the first ankle support. Preferably, a second pair of the ankle retainers flanks the second ankle support and, most preferably, couples to the second ankle support. In some versions, the shield member couples to one or more of the ankle retainers.

Preferably, the second ankle support and the first ankle support couple to each other.

Preferably, the knee support further includes a first leg retainer and a second leg retainer. In some versions, the support base of the knee support has a first end portion and a second end portion. Preferably, the first leg retainer extends upward from the first end portion of the support base. In some versions, the second leg retainer extends upward from the second end portion of the support base.

Preferably, the upward-facing support extends from the first leg retainer to the second leg retainer.

Preferably, the upward-facing support has a width measured transverse to a longitudinal axes of legs of the patient in use with the legs of the patient disposed in the upward-facing support. In some versions, the cradle base has a width measured transverse to the longitudinal axes of legs of the patient in use with the legs of the patient disposed in the first and second ankle supports. Preferably, the width of the support base is at least half as large as the width of the cradle base.

Preferably, the upward-facing support has an upward facing leg-support surface spaced above the bottom surface of the support base by a first height. In some versions, the first ankle support has an upward facing ankle-support surface spaced above the bottom surface of the cradle base by a second height. Preferably, the second height exceeds the first height.

BRIEF DESCRIPTION OF THE DRAWINGS

Preferred versions of the present invention are described in detail below with reference to the following drawings.

DETAILED DESCRIPTION OF THE VARIOUS EMBODIMENTS

Figure 1:
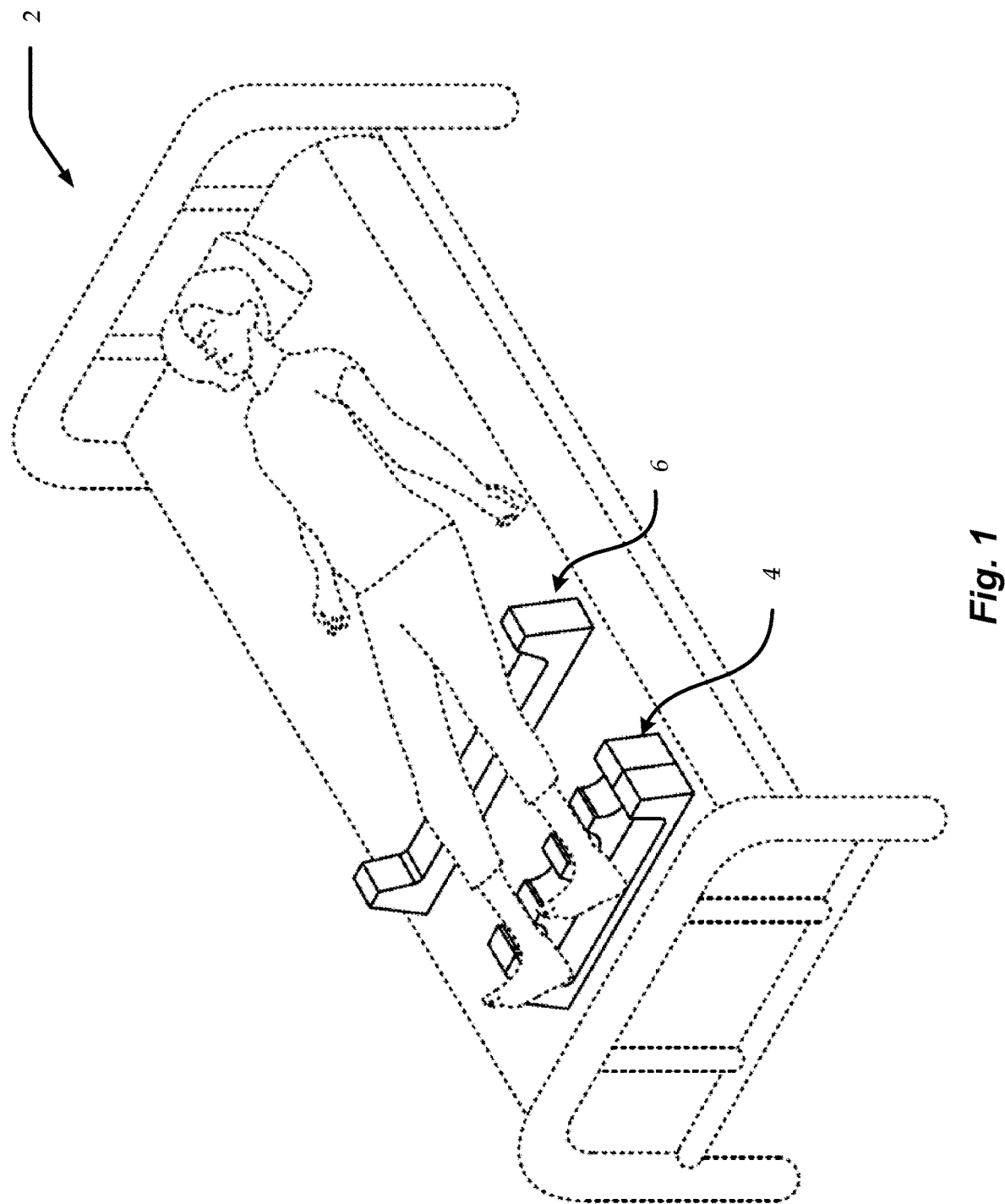
FIG. 1 is an isometric perspective view of a preferred leg support system, including an ankle cradle having a cradle member and a shield member and including a knee support, disposed on a medical support platform.

A preferred leg support system 2 in accordance with the principles of the invention is shown in FIG. 1. As shown in FIG. 1, leg support system 2 is configured to be disposed on a medical support platform, such as a stretcher, spinal board, surgical bed, catheterization laboratory bed, operating room bed, intensive care bed, observation unit bed, inpatient bed, residential bed, or others. Leg support system 2 preferably includes ankle cradle 4 and knee support 6. Ankle cradle 4 and knee support 6 are preferably positioned across the width (the short dimension that is transverse to a human patient's spine) of the medical support platform and spaced apart from each other along the length (the long dimension that is substantially parallel to the patient's spine) of the medical support platform. Accordingly, ankle cradle 4 and knee support 6 are preferably configured to be supported by the same surface of the medical support platform that supports the patient's torso or on the same plane as the portion of the support platform that supports the patient's torso.

The distance between ankle cradle 4 and knee support 6 preferably approximates the distance between the patient's ankles and the patient's knees. The patient's ankles or ankle regions are preferably supported by ankle cradle 4 with the patient's heels suspended in the air, thereby preventing or mitigating pressure ulcers on the patient's heels. The patient's knees or knee regions are preferably supported by knee support 6 with the knees positioned approximately the same elevational distance above the supporting surface of the medical support platform as the ankles. The knees are preferably disposed at an elevation slightly below the elevation of the ankles. Ankle cradle 4 and knee support 6 are sufficiently stable to facilitate placing ankle cradle 4 and knee support 6 on the medical support platform and subsequently, without a medical professional touching ankle cradle 4 or knee support 6, placing the patient's legs in ankle cradle 4 and knee support 6. Accordingly, unlike prior approaches, ankle cradle 4 and knee support 6 may be employed to support the patient's ankles or knees throughout the duration of the patient's treatment, including during surgery or other sterile-environment operation through transport to a recovery location and subsequent thereto.

Figure 2:
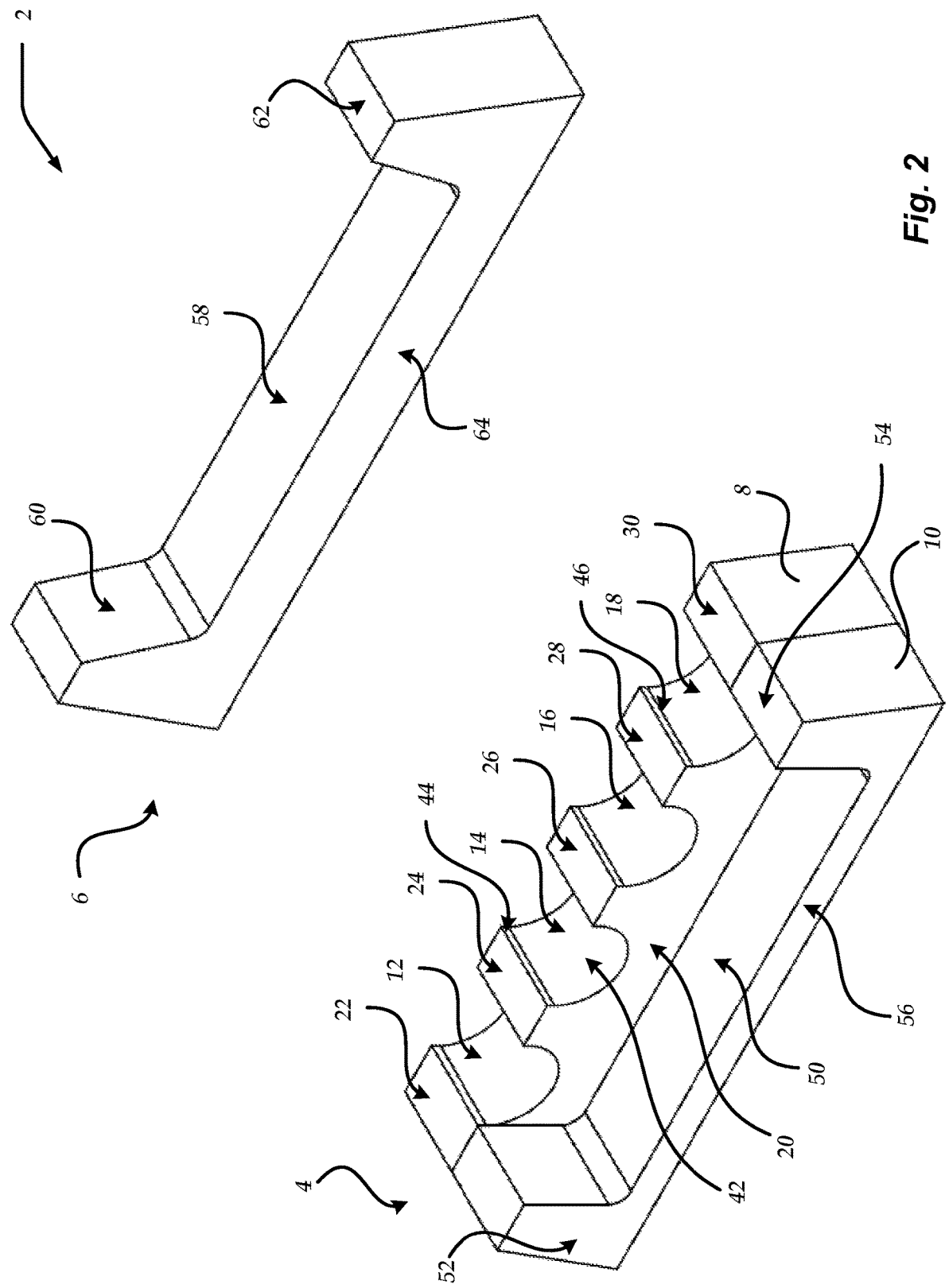
FIG. 2 is an isometric perspective view of the leg support system of FIG. 1.
Figure 8:
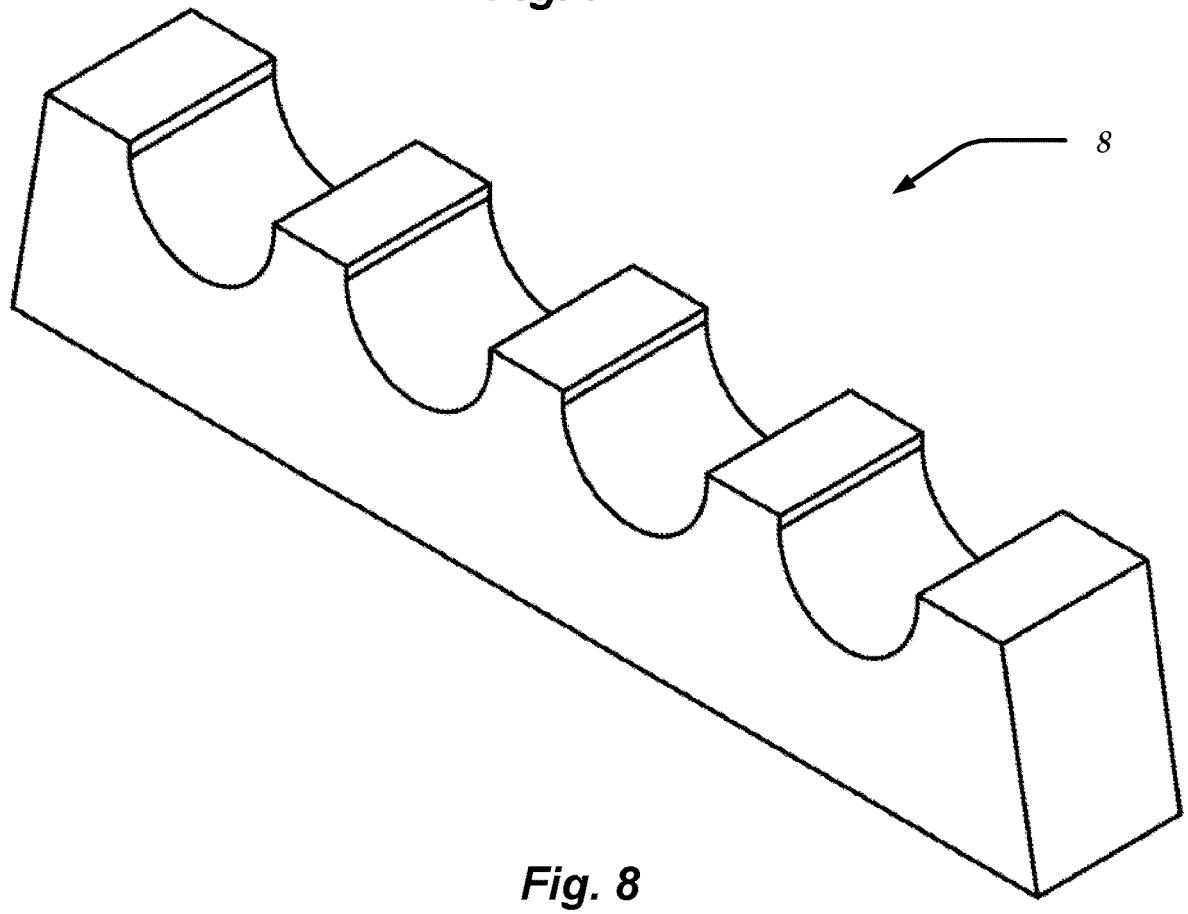
FIG. 8 is an isometric perspective view of the cradle member of FIG. 1.

Ankle cradle 4 preferably includes cradle member 8 and shield member 10 (see FIG. 2). In other versions, ankle cradle 4 is devoid of shield member 10 and consists of cradle member 8 (see FIG. 8). Cradle member 8 preferably has two or more ankle supports (for example, two, three, four, five, or more ankle supports), such as ankle supports 12-18, that are rigidly coupled directly or indirectly to each other through base 20 (for example, fixedly (e.g., adhesively, or others) or separably (e.g., latched, connected via hook-and-loop fasteners, or others) coupled to each other in a rigid relationship to each other) by ankle retainers (for example, ankle retainers 22-30), base 20, or others. As shown in the figures, cradle member 8 is a monolithic structure. The ankle supports are preferably spaced apart from each other by a predefined distance that defines a distance between the patient's legs (i.e., a distance by which the patient's legs are spaced apart). In versions having more than two ankle supports, the ankle supports are preferably arranged such that a line (for example, a straight or arched line) intersects each of the ankle supports. This arrangement facilitates the medical professional placing one of the patient's legs in one of the ankle supports (for example, an outermost ankle support) and selecting another ankle support in which to place the patient's other leg, thereby selecting a predefined distance to maintain between the patient's legs.

Each ankle support is preferably flanked by two ankle retainers (for example, ankle retainers 22-30) that facilitate retaining the selected lateral positions (for example, the selected positions along the long dimension of cradle member 8) of the patient's legs. Each ankle support preferably shares an ankle retainer with another ankle support (for example, ankle support 12 shares ankle retainer 24 with ankle support 14; as another example, ankle supports 14, 16 and ankle retainer 26 may be omitted, and ankle retainers 24, 28 may be replaced with a single ankle retainer that extends from ankle support 12 to ankle support 18). In other versions, the ankle retainers of two sequentially positioned ankle supports that are closest to each other may be spaced apart from each other (for example, ankle supports 14, 16 and ankle retainer 26 may be omitted, and only base 20 couples ankle retainer 24 to ankle retainer 28).

The ankle-contacting surfaces (for example, ankle-contacting surface 42) of the ankle supports are preferably radiused to facilitate distributing the pressure applied to the ankles. The ankle retainers preferably have retaining sidewalls (for example, retaining sidewall 44) that extends above the equator of the radiuses (for example, equator 46), which is preferably parallel to bottom surface 48 of cradle member 8 (see FIG. 4). The retaining sidewalls are preferably flat, and most preferably perpendicular to bottom surface 48 of cradle member 8, to facilitate providing further lateral guidance when placing the patient's legs in the ankle supports without encroaching on the openings of the ankle supports.

Shield member 10 preferably has one or more lower shields (for example, lower shield 50) that are each flanked by two side shields (for example, side shields 52, 54). Shield base 56 preferably couples the lower shields to each other and preferably couples the side shields to each other. As shown in the figures, shield member 10 is a monolithic structure. Cradle member 8 and shield member 10 may be integral or coupled to each other (for example, fixedly or separably).

Knee support 6 preferably has only a single upward-facing support (for example, upward-facing support 58) that facilitates slidably positioning each of the patient's legs along the lateral dimension of knee support 6 (for example, the long dimension of knee support 6) when placing the patient's legs in the selected ankle supports. Upward-facing support 58 is preferably flanked by two leg retainers 60, 62 that are coupled to each other by base member 64 and that facilitate preventing the patient's legs from sliding off upward-facing support 58 without employment of a member (for example, a rolled-up sheet) tied around the patient's knees or other portions of the legs, as is the present standard of care.

Open-cell foam blocks (most preferably, open-cell memory foam blocks) are preferably cut to form knee support 6, cradle member 8, and shield member 10 as monolithic structures. Cradle member 8 and shield member 10 are preferably coupled to each other to form ankle cradle 4. In some versions, one or more of the components are formed by injection molding. One or more portions of one or more of the components is preferably covered in elastomeric material, such as neoprene.

Figure 3:
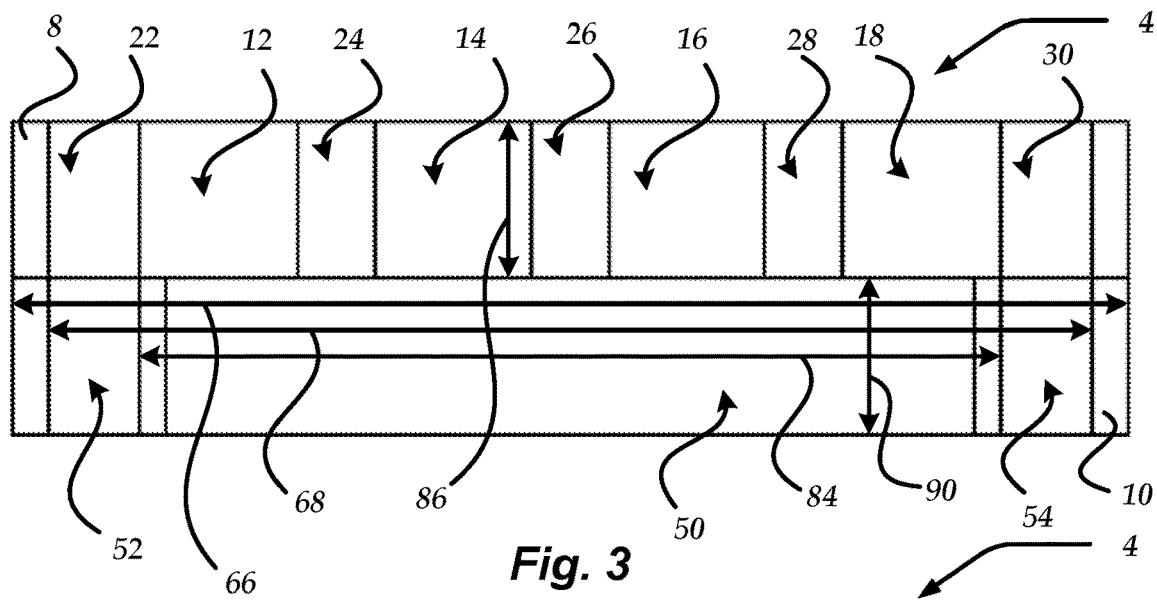
FIG. 3 is an isometric overhead view of the ankle cradle of FIG. 1.
Figure 4:
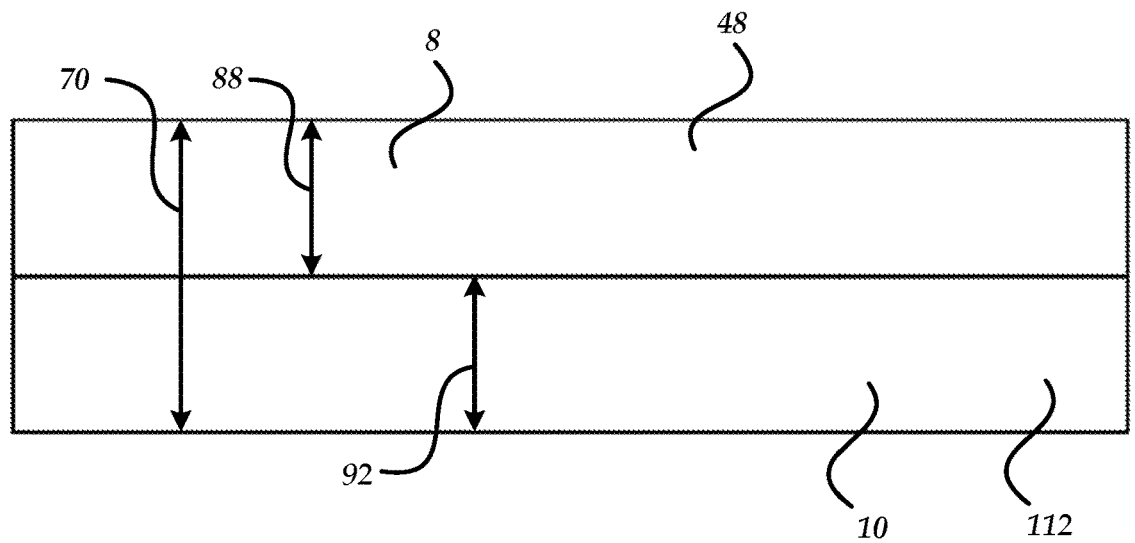
FIG. 4 is an isometric underside view of the ankle cradle of FIG. 1.
Figure 5:
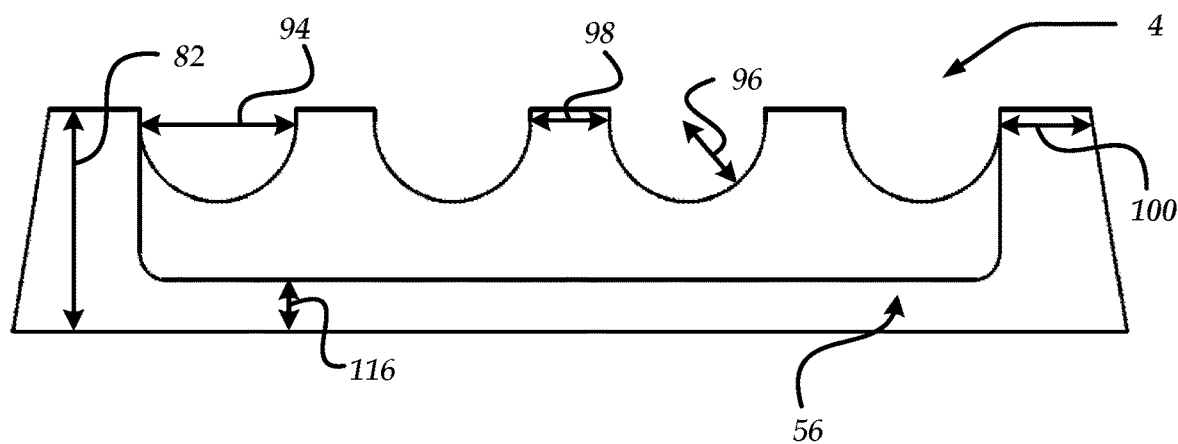
FIG. 5 is an isometric elevational view of the ankle cradle of FIG. 1.

As shown in FIGS. 3-5, ankle cradle 4 preferably has bottom width 66 (for example, 18, 21, or 24 inches, more or less than any one of those values, or any number of inches between any two of those values), top width 68 (for example, 17, 20, or 22 inches, more or less than any one of those values, or any number of inches between any two of those values), length 70 (for example, 6 inches, or more or less than that value), and height 82 (for example, 3 or 4 inches, more or less than any one of those values, or any number of inches between those values). Cradle member 8 and shield member 10 preferably have the approximately the same values for their respective bottom widths, top widths, lengths, and heights. Shield member 10 preferably has distance 84 between the outermost side shields (for example, 14, 16, or 19 inches, more or less than any one of those values, or any number of inches between any two of those values). Cradle member 8 preferably has the approximately the same distance between the outermost ankle retainers as distance 84. The ankle supports preferably have approximately the same upper length (for example, upper length 86) that approximately matches bottom length 88 of cradle member 8, one or both of which preferably approximately match upper length 90 of shield member 10, which preferably approximately matches bottom length 92 of cradle member 10.

As shown in FIG. 5, each ankle support preferably has a maximal width (for example, maximal width 94, which may have a magnitude of 2, 3, or 4 inches, more or less than any one of those values, or any number of inches between any two of those values) defined by the width of the equator of the ankle support. The maximal widths of the ankle supports are preferably approximately the same as each other. Each ankle support preferably has a radius (for example, radius 96) that approximately matches half of the maximal width of the ankle support. Each ankle retainer preferably has an upper width (for example, upper width 98, which may have a magnitude of 1, 1.5, or 2 inches, more or less than any one of those values, or any number of inches between any two of those values) that approximately matches the upper width of each other ankle retainer. Each side shield preferably has an upper width (for example, upper width 100, which may have a magnitude of 1, 1.5, or 2 inches, more or less than any one of those values, or any number of inches between any two those values) that approximately matches the upper width of each other side shield. The ankle retainers preferably have upper widths that approximately match the respective side shields with which the ankle retainers laterally correspond (for example, the outermost ankle retainers may have upper widths that are approximately the same as the upper widths of the outermost side shields).

Figure 6:
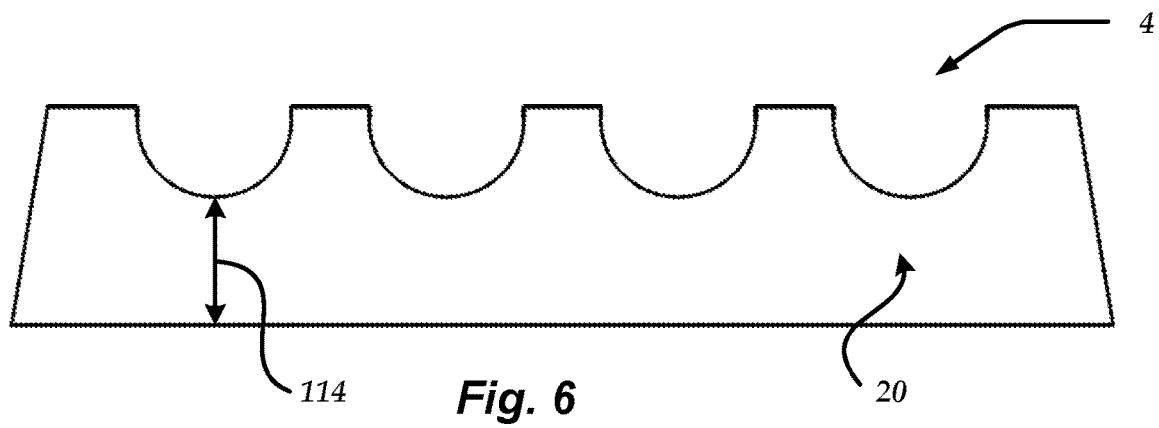
FIG. 6 is an isometric elevational view of the ankle cradle of FIG. 1.
Figure 7:
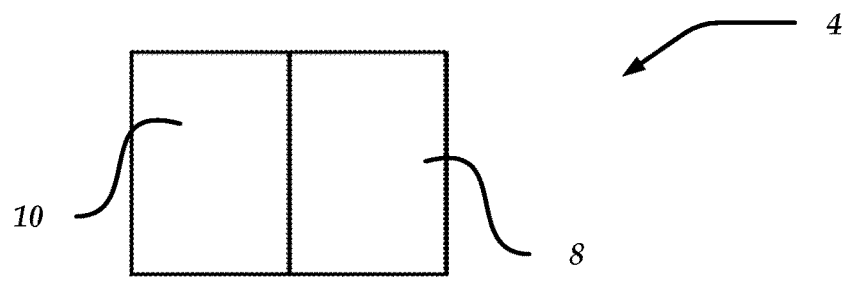
FIG. 7 is an isometric side elevational view of the ankle cradle of FIG. 1.

As shown in FIGS. 5 and 6, base member 20 of cradle member 8 preferably extends from bottom surface 48 of cradle member 8 to the upward facing surfaces of the ankle supports, and base member 56 of shield member 10 preferably extends from bottom surface 112 of shield member 10 to the one or more upward facing surfaces of the one or more lower shields. Base member 20 preferably has height 114, which may have a magnitude of 1.75 or 2.5 inches, more or less than one of those values, or any number of inches between those values. Base member 56 preferably has height 116, which may have a magnitude of 0.5 or 1 inches, more or less than one of those values, or any number of inches between those values.

Figure 9:
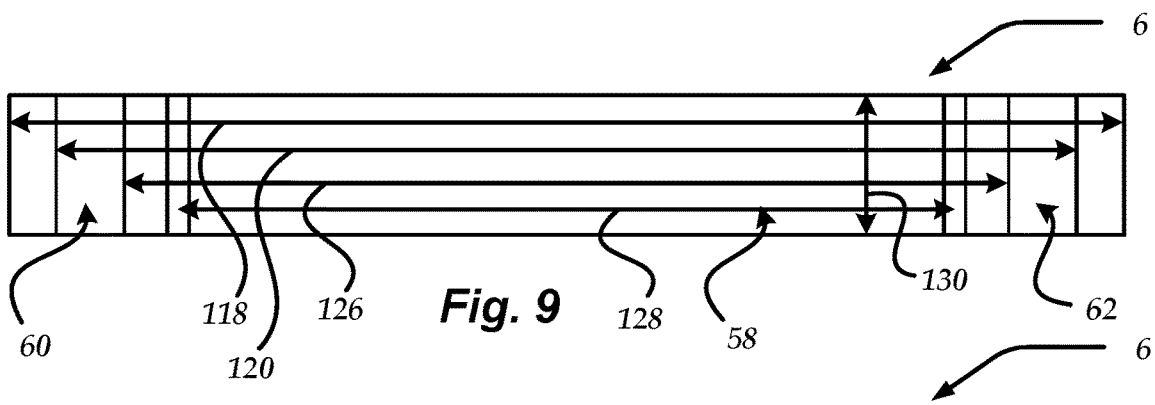
FIG. 9 is an isometric overhead view of the knee support of FIG. 1.
Figure 10:
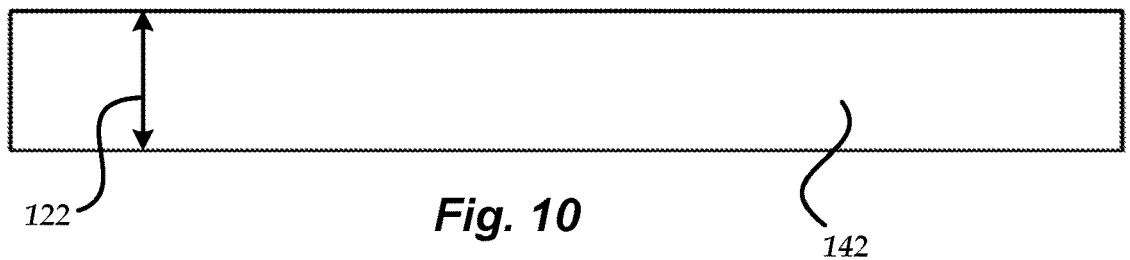
FIG. 10 is an isometric underside view of the knee support of FIG. 1.
Figure 11:
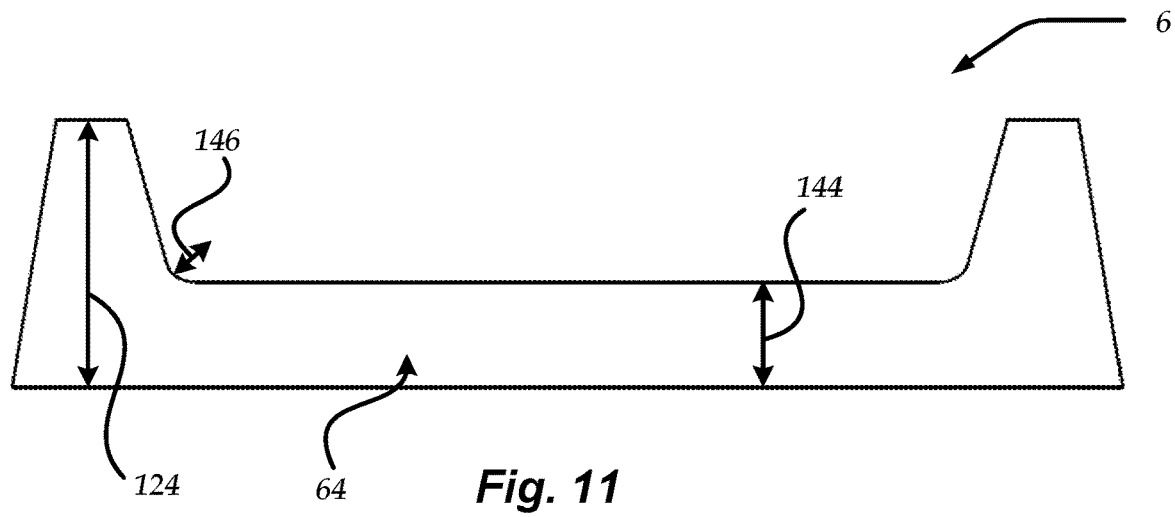
FIG. 11 is an isometric elevational view of the knee support of FIG. 1.
Figure 12:
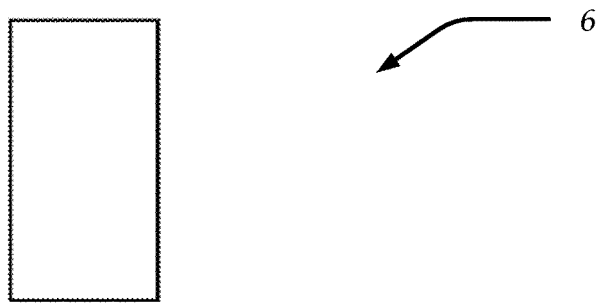
FIG. 12 is an isometric side elevational view of the knee support of FIG. 1.
Figure 13:
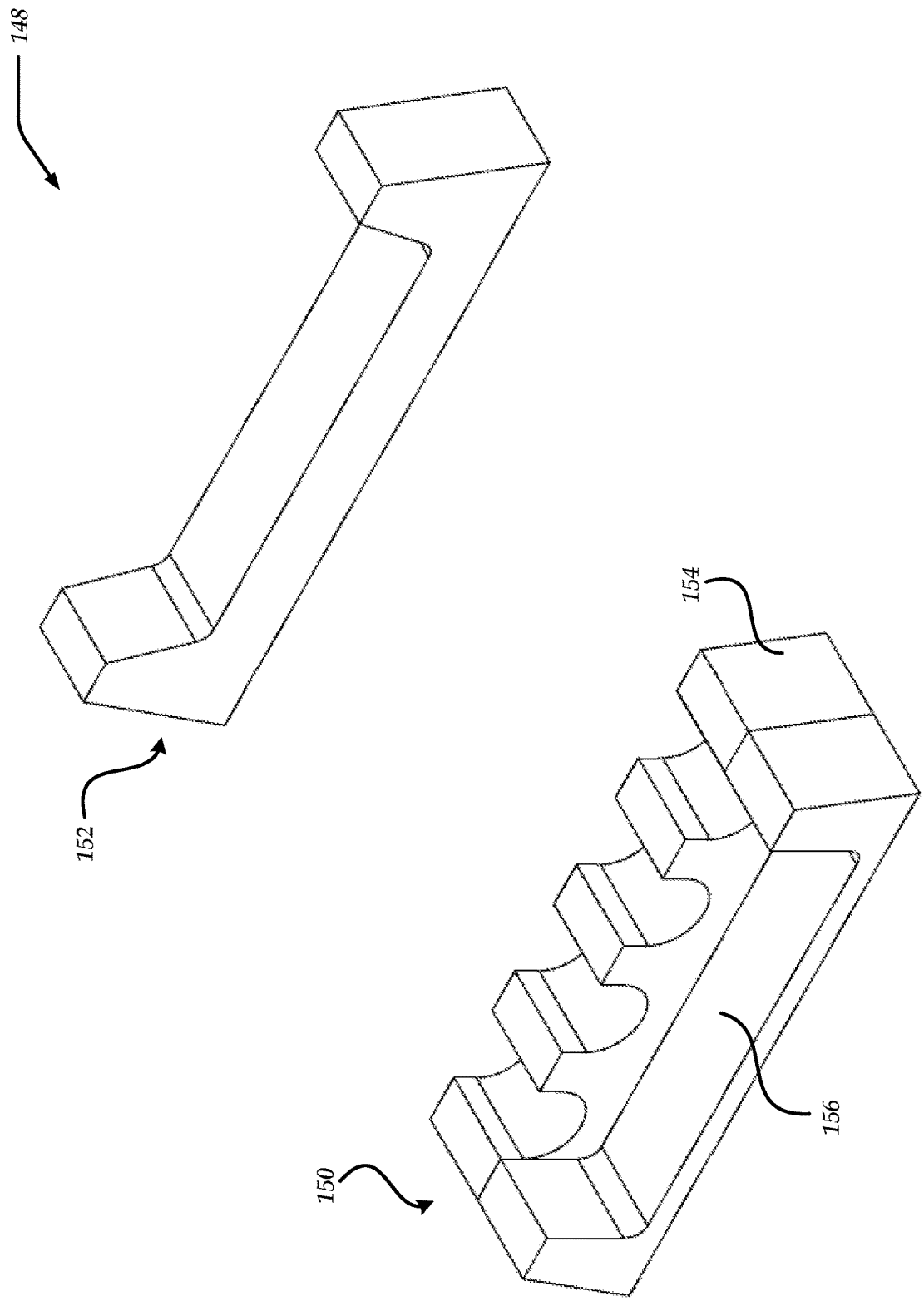
FIG. 13 is an isometric perspective view of a preferred leg support system, including an ankle cradle having a cradle member and a shield member and including a knee support.
Figure 14:
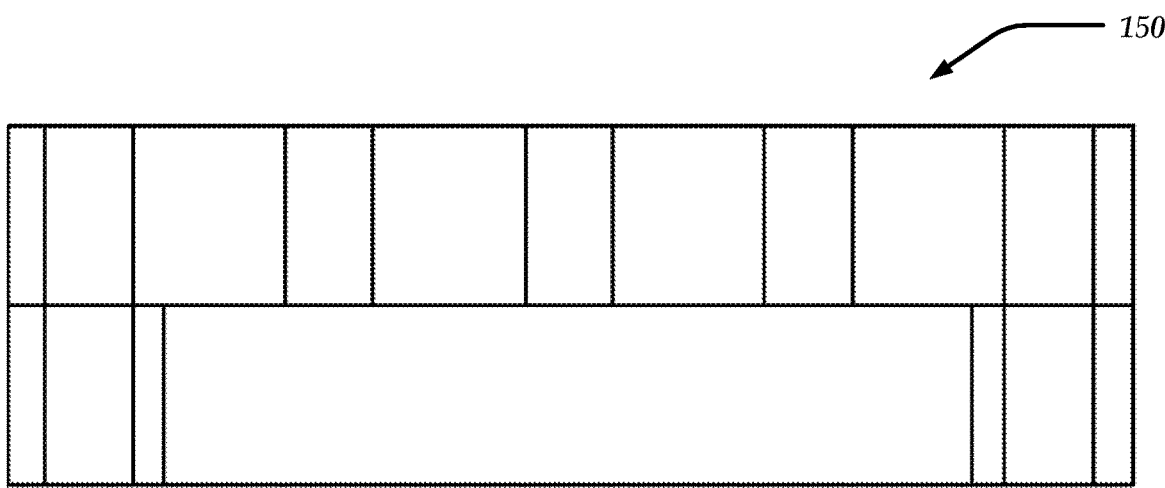
FIG. 14 is an isometric overhead view of the ankle cradle of FIG. 13.
Figure 15:
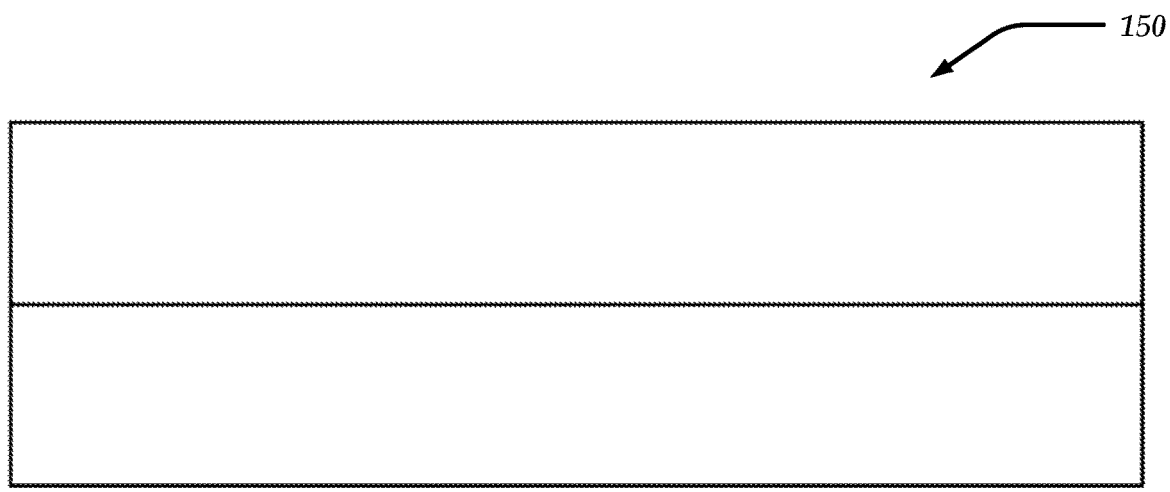
FIG. 15 is an isometric underside view of the ankle cradle of FIG. 13.
Figure 16:
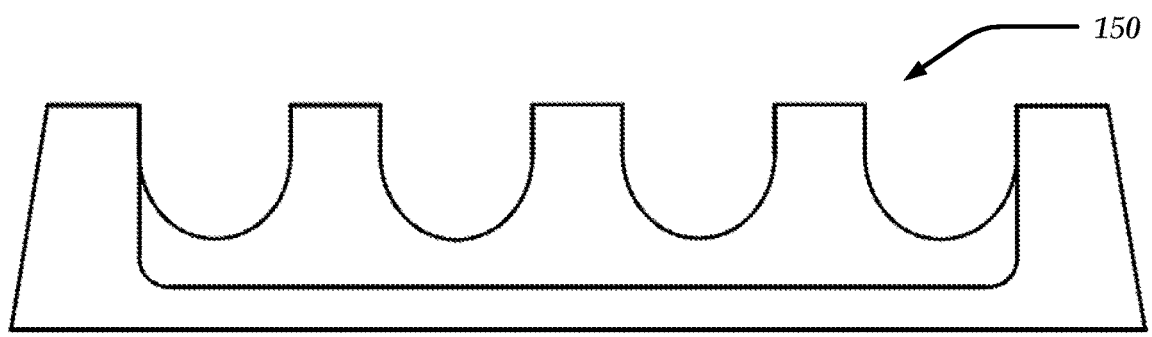
FIG. 16 is an isometric elevational view of the ankle cradle of FIG. 13.
Figure 17:
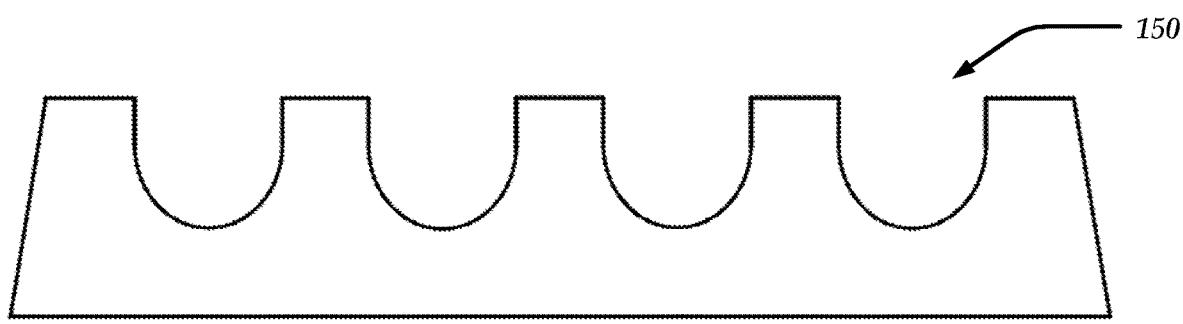
FIG. 17 is an isometric elevational view of the ankle cradle of FIG. 13.
Figure 18:
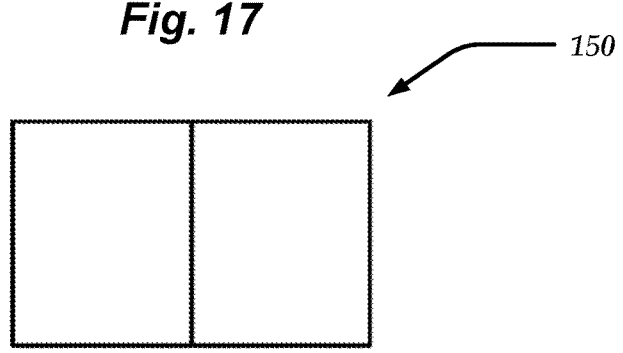
FIG. 18 is an isometric side elevational view of the ankle cradle of FIG. 13.
Figure 19:
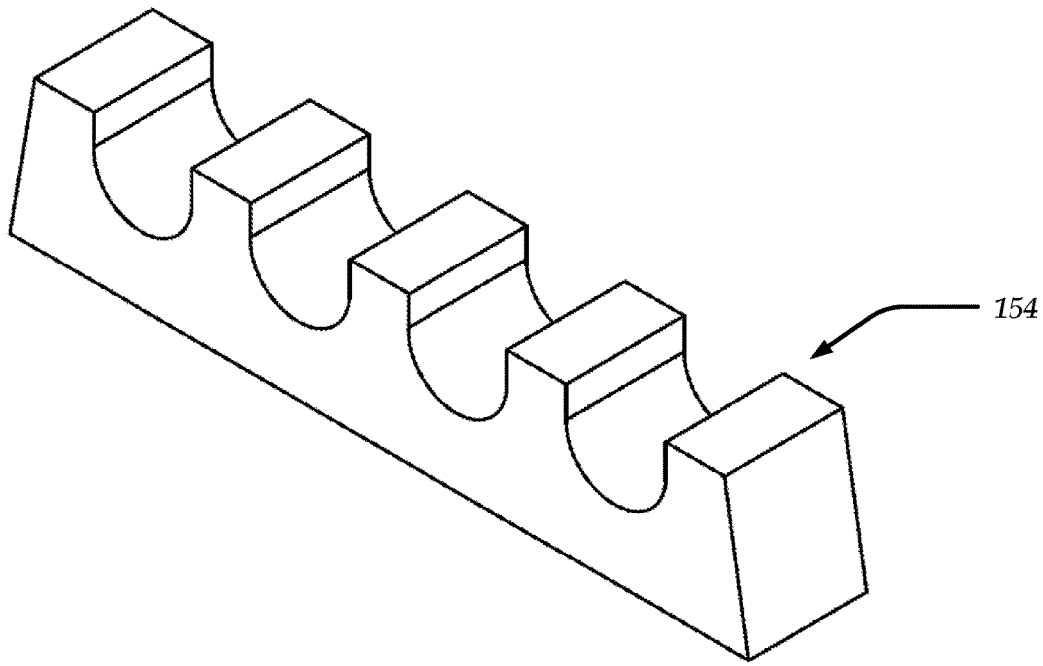
FIG. 19 is an isometric perspective view of the cradle member of FIG. 13.
Figure 20:
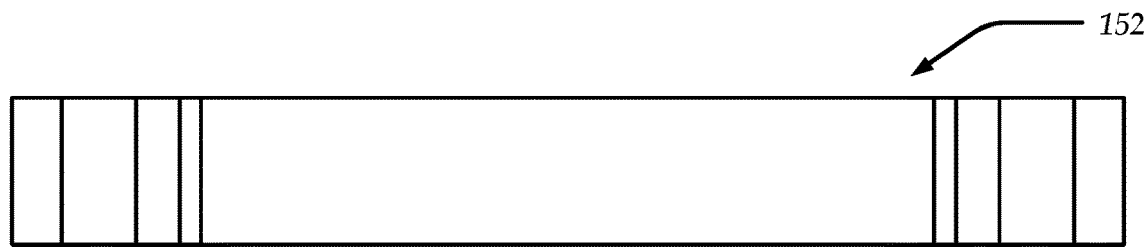
FIG. 20 is an isometric overhead view of the knee support of FIG. 13.
Figure 21:
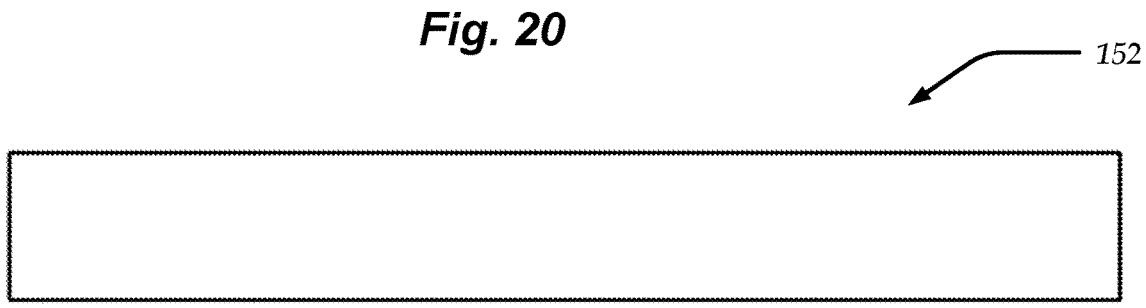
FIG. 21 is an isometric underside view of the knee support of FIG. 13.
Figure 22:
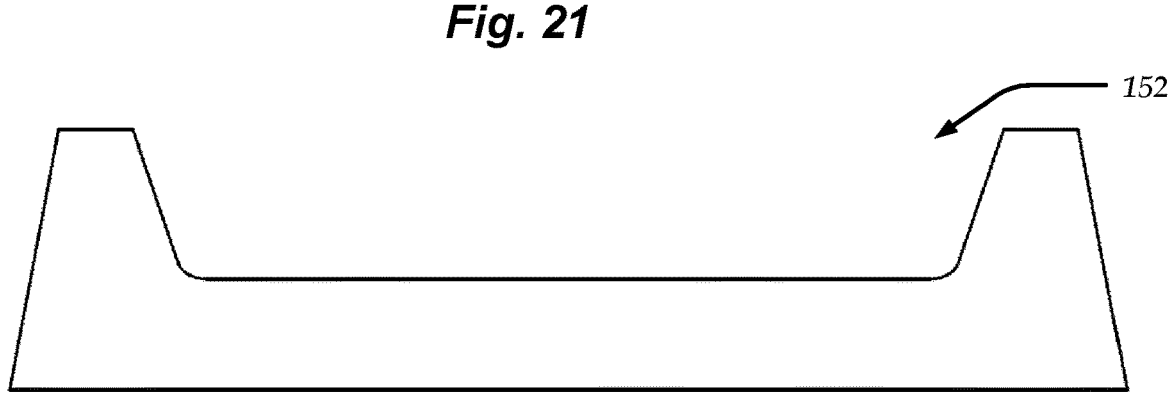
FIG. 22 is an isometric elevational view of the knee support of FIG. 13.
Figure 23:
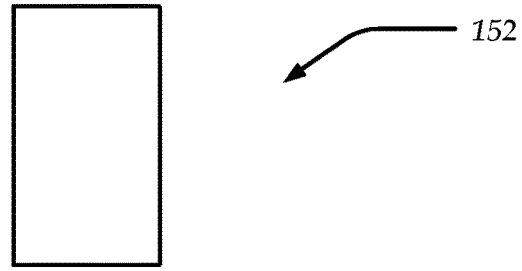
FIG. 23 is an isometric side elevational view of the knee support of FIG. 13.

As shown in FIGS. 9-11, knee support 6 preferably has bottom width 118 (for example, 22 or 24 inches, more or less than any one of those values, or any number of inches between those values), top width 120 (for example, 20 or 22 inches, more or less than any one of those values, or any number of inches between those values), length 122 (for example, 3 inches or more or less inches), and height 124 (for example, 5 or 6 inches, more or less than any one of those values, or any number of inches between those values). Leg retainers 60, 62 are preferably spaced apart from each other by one or more distances, such as upper distance 126 (for example, 17 or 19 inches, more or less than any one of those values, or any number of inches between those values) and lower distance 128 (for example, 15 or 17 inches, more or less than any one of those values, or any number of inches between those values). Upward-facing support 58 has upper length 130 (for example, 3 inches or more or less than that value) that approximately matches bottom length 122 of knee support 6. As shown in FIG. 11, base member 64 preferably extends from bottom surface 142 of knee support 6 to the upward-facing surface of upward-facing support 58 and preferably has height 144, which may have a magnitude of 2 inches or more or less than that value. The transition between leg retainers 60, 62 and upward-facing support 58 is preferably radiused and may have a radius, such as radius 146, of 0.5 inches or more or less than that value.

The components of leg support system 2 are preferably sized and dimensioned to scale as shown in FIGS. 2-12. FIGS. 13-23 also show a preferred leg support system 148 in accordance with the principles of the invention yet with one or more of the components of leg support system 148 being sized and dimensioned different than one or more of the corresponding components of leg support system 2. Leg support system 148 preferably includes ankle cradle 150 and knee support 152. Ankle cradle 150 preferably includes cradle member 154 and shield member 156. In other versions, ankle cradle 150 is devoid of shield member 156 and consists of cradle member 154 (see FIG. 23). Any combination of the dimensions described relative to one or more components of leg support system 2 may be applied to any one or more components of leg support system 2. The components of leg support system 148 are preferably sized and dimensioned to scale as shown in FIGS. 13-23. However, any one or more of the dimensions disclosed herein or others may be applied to any one or more of the corresponding components of leg support system 2 or leg support system 148 in combination with any one or more of the other dimensions disclosed herein or others applied to any one or more of the other corresponding components of leg support system 2 or leg support system 148.

As used herein, the following terms take the meanings explicitly associated herein, unless the context clearly dictates otherwise. The term "or" is an inclusive grammatical conjunction to indicate that one or more of the connected terms may be employed. For example, the phrase "one or more A, B, or C" or the phrase "one or more As, Bs, or Cs" is employed to discretely disclose each of the following: i) one or more As, ii) one or more Bs, iii) one or more Cs, iv) one or more As and one or more Bs, v) one or more As and one or more Cs, vi) one or more Bs and one or more Cs, and vii) one or more As, one or more Bs, and one or more Cs. The term "based on" as used herein is not exclusive and allows for being based on additional factors not described. The articles "a," "an," and "the" include plural references. Plural references are intended to also disclose the singular.

The term "longitudinal" or "length" and related terms are defined relative to the medical support platform when the leg support system is installed on the medical support platform (for example, as shown in FIG. 1). The longitudinal axis of the medical support platform extends from one end of the medical support platform to the opposite end of the medical support platform along its major dimension. The term "height," "upper," "upward," "lower," "downward," "top," or "bottom" and related terms are defined relative to the vertical axis of the medical support platform when the leg support system is installed on the medical support platform. The vertical axis extends transversely and preferably perpendicular to the supporting surface of the medical support platform and is defined as parallel to the direction of the earth's gravity force on the medical support platform or the relevant component of the leg support system when the medical support system is on horizontal ground. The term "lateral" or "width" and related terms are defined relative to the lateral axis of the medical support surface or the relevant component of the leg support system when installed on the medical support surface. The lateral axis is transverse to the longitudinal and vertical axes.

The terms "approximate" or "slightly" and related terms are defined as the same as the corresponding value or within 30, 25, 20, 15, 10, or 5 percent of the corresponding value. The term "configured" refers to sized, dimensioned, positioned, or oriented.

Notably, medical support platforms are of various shapes and sizes. Accordingly, some features or characteristics of the present invention are best understood by one of ordinary skill in the art when defined relative to one or more elements that are related to yet are not comprised in the present invention, such as one or more features or characteristics of medical support platforms. Also accordingly, where features or characteristics of the present invention are defined herein relative to one or more elements that are related to yet are not comprised in the present invention, such definitions are as accurate as the subject matter permits. It should also be noted that one of ordinary skill in the art realizes from the present disclosure that those features or characteristics of the present invention could be easily obtained according to the principles of the present invention for a given medical support platforms or other related element that is not comprised in the present invention.

While the preferred embodiment of the invention has been illustrated and described, as noted above, many changes can be made without departing from the spirit and scope of the invention. For example, each disclosure of a component preferably having a feature or characteristic is intended to also disclose the component as being devoid of that feature or characteristic, unless the principles of the invention clearly dictate otherwise. Accordingly, the scope of the invention is not limited by the disclosure of the preferred embodiment. Instead, the invention should be determined entirely by reference to the claims that follow.

What is claimed is:

1. A leg support system for preventing or mitigating pressure ulcers on heels of a patient supported on a top surface of a medical support platform, the leg support system comprising:
    a knee support, the knee support including:
        a support base having a bottom surface and being sized and dimensioned to be supported on a top surface of a medical support platform that supports a patient, with the bottom surface of the support base contacting the top surface of the medical support platform; and
        an upward-facing support disposed on the support base; and
    an ankle cradle, the ankle cradle including:
        a cradle base having a bottom surface and being sized and dimensioned to be supported on the top surface of the medical support platform, with the bottom surface of the cradle base contacting the top surface of the medical support platform;
        a first ankle support coupled to the cradle base; and
        a second ankle support spaced apart from the first ankle support and being coupled to the first ankle support or the cradle base,
    wherein the upward-facing support has an upward facing leg-support surface spaced above the bottom surface of the support base by a first height, the first ankle support having an upward facing ankle-support surface spaced above the bottom surface of the cradle base by a second height, the second height exceeding the first height.

2. The leg support system of claim 1, wherein the ankle cradle further includes a third ankle support spaced apart from the first ankle support and the second ankle support and coupled to the first ankle support, the second ankle support, or the cradle base.

3. The leg support system of claim 1, wherein the ankle cradle further includes three or more ankle retainers, a first pair of the ankle retainers flanking the first ankle support, a second pair of the ankle retainers flanking the second ankle support.

4. The leg support system of claim 1, wherein the ankle cradle further includes a shield member, the first ankle support and the second ankle support forming a cradle member, the cradle member having a first side and a second side and being sized and dimensioned such that, when ankles of the patient are supported in the first ankle support and the second ankle support, heels of the patient are suspended on the first side of the cradle member and a torso of the patient is disposed on the second side of the cradle member, the shield member being coupled to the cradle member or the cradle base, being disposed on the first side of the cradle member, and being spaced apart from the first ankle support and the second ankle support.

5. The leg support system of claim 4, wherein the shield member includes a shield base, the cradle base forming a base of the cradle member, the shield base of the shield member being coupled to the cradle base of the cradle member.

6. The leg support system of claim 4, wherein the cradle member has three or more ankle retainers, a first pair of the ankle retainers flanking the first ankle support, a second pair of the ankle retainers flanking the second ankle support, the shield member being coupled to one or more of the ankle retainers.

7. The leg support system of claim 1, wherein the second ankle support and the first ankle support are coupled to each other.

8. The leg support system of claim 1, wherein the knee support further includes a first leg retainer and a second leg retainer, the support base of the knee support having a first end portion and a second end portion, the first leg retainer extending upward from the first end portion of the support base, the second leg retainer extending upward from the second end portion of the support base, the upward-facing support extending from the first leg retainer to the second leg retainer.

9. The leg support system of claim 8, wherein the upward-facing support has a width measured transverse to a longitudinal axes of legs of the patient in use with the legs of the patient disposed in the upward-facing support, the cradle base having a width measured transverse to the longitudinal axes of legs of the patient in use with the legs of the patient disposed in the first and second ankle supports, the width of the support base being at least half as large as the width of the cradle base.

10. An ankle cradle for preventing or mitigating pressure ulcers on heels of a patient supported on a top surface of a medical support platform, the ankle cradle comprising:
- a cradle base having a bottom surface and being sized and dimensioned to be supported on a top surface of a medical support platform that supports a patient, with the bottom surface of the cradle base contacting the top surface of the medical support platform;
- a first ankle support coupled to the cradle base;
- a second ankle support spaced apart from the first ankle support and coupled to the first ankle support or the cradle base; and
- a third ankle support spaced apart from the first ankle support and the second ankle support and coupled to the first ankle support, the second ankle support, or the cradle base.

11. The ankle cradle of claim 10, further comprising three or more ankle retainers, a first pair of the ankle retainers flanking the first ankle support, a second pair of the ankle retainers flanking the second ankle support.

12. The ankle cradle of claim 10, further comprising a shield member, the first ankle support and the second ankle support forming a cradle member, the cradle member having a first side and a second side and being sized and dimensioned such that, when ankles of the patient are supported in the first ankle support and the second ankle support, heels of the patient are suspended on the first side of the cradle member and a torso of the patient is disposed on the second side of the cradle member, the shield member being coupled to the cradle member or the cradle base, being disposed on the first side of the cradle member, and being spaced apart from the first ankle support and the second ankle support.

13. The ankle cradle of claim 12, wherein the shield member includes a shield base, the cradle base forming a base of the cradle member, the shield base of the shield member being coupled to the cradle base of the cradle member.

14. The ankle cradle of claim 12, wherein the cradle member has three or more ankle retainers, a first pair of the ankle retainers flanking the first ankle support, a second pair of the ankle retainers flanking the second ankle support, the shield member being coupled to one or more of the ankle retainers.

15. The ankle cradle of claim 10, wherein the first ankle support and the second ankle support are spaced apart from each other along a lateral dimension and extend above the cradle base in a vertical dimension that is transverse to the lateral dimension, the first ankle support and the second ankle support having respective lengths as measured transverse to the lateral dimension and the vertical dimension, the lengths of the first ankle support and the second ankle support being approximately 3 inches or less.

16. An ankle cradle for preventing or mitigating pressure ulcers on heels of a patient supported on a top surface of a medical support platform, the ankle cradle comprising:
- a cradle base having a bottom surface and being sized and dimensioned to be supported on a top surface of a medical support platform that supports a patient, with the bottom surface of the cradle base contacting the top surface of the medical support platform;
- a first ankle support coupled to the cradle base;
- a second ankle support spaced apart from the first ankle support and coupled to the first ankle support; and
- a shield member, the first ankle support and the second ankle support forming a cradle member, the cradle member having a lateral dimension, the first ankle support and the second ankle support being spaced apart from each other along the lateral dimension of the cradle member, the cradle member having a first side and a second side and being sized and dimensioned such that, when ankles of the patient are supported in the first ankle support and the second ankle support, heels of the patient are suspended on the first side of the cradle member and a torso of the patient is disposed on the second side of the cradle member, the shield member being coupled to the cradle member, being disposed on the first side of the cradle member, and extending along the longitudinal dimension of the cradle member, each portion of the shield member that aligns with one of the first ankle support or the second ankle support along the lateral dimension of the cradle member being disposed entirely below the one of the first ankle support or the second ankle.

17. The ankle cradle of claim 16, further comprising a third ankle support disposed on the cradle base, spaced apart from the first ankle support and the second ankle support, and coupled to the first ankle support and the second ankle support.

18. The ankle cradle of claim 16, wherein the first ankle support defines a first ankle-contacting surface, the second ankle support defining a second ankle-contacting surface, the first ankle-contacting surface and the second ankle-contacting surface being radiused.

19. The ankle cradle of claim 16, wherein the first ankle support and the second ankle support are spaced apart from each other along a lateral dimension and extend above the cradle base in a vertical dimension that is transverse to the lateral dimension, the first ankle support and the second ankle support having respective lengths as measured transverse to the lateral dimension and the vertical dimension, the shield member having a length as measured parallel to the lengths of the first ankle support and the second ankle support, the lengths of the first ankle support and the second ankle support being approximately the same as the length of the shield member.

* * * * *